United States Patent [19]

Giguere et al.

[11] Patent Number: 5,760,220

[45] Date of Patent: Jun. 2, 1998

[54] PROCESS FOR PREPARATION OF BIPHENYL DERIVATIVES

[75] Inventors: Pierre Giguere, Dorothee; Silvio Iera; Michel Bernatchez, both of Montreal, all of Canada; Giuseppe Barreca, Milan, Italy; Graziano Castaldi, Briona, Italy; Vincenzo Cannata, Marconi, Italy

[73] Assignee: American Home Products Corporation, Madison, N.J.

[21] Appl. No.: 657,490

[22] Filed: Jun. 4, 1996

[51] Int. Cl.$^6$ .............. C07D 471/04; C07D 487/04; C07D 257/04

[52] U.S. Cl. .............. 540/521; 540/461; 544/279; 544/280; 548/103

[58] Field of Search .............. 544/262, 279, 544/280; 540/521, 461; 548/103

[56] References Cited

U.S. PATENT DOCUMENTS

| | | | |
|---|---|---|---|
| 5,039,814 | 8/1991 | Shuman et al. | 548/250 |
| 5,149,699 | 9/1992 | Ellingboe et al. | 514/258 |
| 5,466,692 | 11/1995 | Ellingboe et al. | 514/258 |

FOREIGN PATENT DOCUMENTS

| | | |
|---|---|---|
| 0497150 | 8/1992 | European Pat. Off. |
| 0550313 | 12/1992 | European Pat. Off. |

OTHER PUBLICATIONS

E. Negishi et al., J. Org. Chem. 42, 1821 (1977).
J.E. Tilley et al., J. Med. Chem., 32, 1814 (1989).
A.S. Bell et al., Synthesis, 843 (1987).

*Primary Examiner*—John M. Ford
*Attorney, Agent, or Firm*—Arthur G. Seifert

[57] ABSTRACT

A process is described for preparing a compound of the formula I:

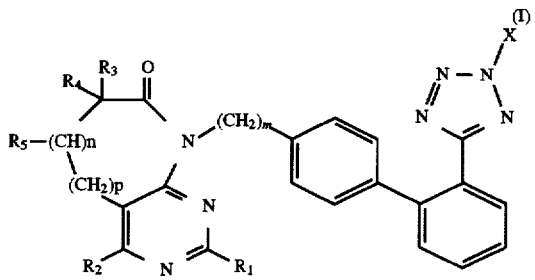

or a salt thereof;

wherein X is a protecting group and $R_1$, $R_2$, $R_3$ and $R_4$ are each independently hydrogen, $C_{1-6}$ alkyl or $C_{1-6}$ perfluoroalkyl, $R_5$ is hydrogen or when n is 1 $R_5$ taken together with $R_3$ comprises a double bond; m is 1, 2 or 3; n is 0 or 1, and p is 0, 1 or 2.

46 Claims, No Drawings

PROCESS FOR PREPARATION OF BIPHENYL DERIVATIVES

This invention concerns an improved process for production of inter alia the intermediate 8-[2'-(2(1)-tert-butyl-2H-tetrazol-5-yl)-biphenyl-4-yl-methyl]-2,4-di-methyl-5,8-dihydro-6H-pyrido[2,3-d]pyrimidin-7-one, which is the precursor to the product drug substance 5,8-dihydro-2,4-dimethyl-8-[(2'-(1H-tetrazol-5-yl)[1,1'-biphenyl]- Said product drug substance is an angiotensin II antagonist, particularly useful as an antihypertensive agent, which is disclosed in U.S. Pat. No. 5,149,699 (American Home Products Corporation).

The following abbreviations are used herein:

| Abbreviation | Full name |
| --- | --- |
| acac | acetonylacetone |
| dba | dibenzylidene acetone |
| DIBAL | diisobutyl aluminium hydride |
| DME | dimethoxyethane |
| DPPB | bis(1,4-diphenylphosphino)butane |
| dppe | diphenylphosphinoethane |
| DPPP | 1,3-(diphenylphosphino)propane |
| OAc | acetoxy |
| OiPr | isopropoxy |
| trityl | triphenylmethyl |

BACKGROUND OF THE INVENTION

E. Negishi, A. O. King and N. Okukado, J. Org. Chem. 42, 1821 (1977), disclosed that the cross-coupling of aryl- and benzylzinc derivatives with aryl bromides or iodides in the presence of catalytic amounts of a Ni or Pd catalyst provided a general and highly chemo- and regioselective synthetic route to unsymetrical biaryls and diarylmethanes, with the amounts of the homocoupled biaryls being less than five percent. J. W. Tilley, J. W. Clader, S. Zawoiski, M. Wirkus, R. A. LeMahieu, M. O'Donnell, H. Crowley & A. F. Welton; J. Med. Chem. 32, 1814 (1989), show an example of a Negishi cross-coupling in Scheme II on page 1816 and in the Experimental Section in column 2, page 1818, second example in which 2-bromo-3',4'-dimethoxy-1,1'-biphenyl-4-carboxylic acid methyl ester is prepared. In this example the 3,4-dimethoxyphenylzinc reactant is made by reacting butyllithium with 3,4-dimethoxybrombenzene, followed by transmetallation with zinc chloride. The cross-coupling catalyst is bis(triphenylphoshine)palladium dichloride. A. S. Bell, D. A. Roberts & K. S. Ruddock; Synthesis 843 (1987), report the direct synthesis of 6-pyridinyl-2(1H)-quinolinones by palladium-catalyzed cross-coupling of pyridinylzinc chlorides with haloquinolinones. The pyridinylzinc chloride reagents are obtained by transmetallation of pyridinyllithium or pyridinylmagnesium halides with zinc chloride.

The references above describe the preparation of arylzinc derivative and their palladium catalyzed cross-coupling with aryl halides to afford biphenyl compounds. However, none of these references described the use of aryltetrazoles in the cross-coupling reaction or the preparation of a biphenyl tetrazoles.

U.S. Pat. No. 5,039,814 (Merck & Co.) describes the production of ortho-lithiated aryltetrazoles of structure

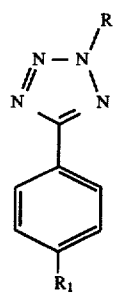

R₁ = H, t-butyl, phenoxy
R₂ = H or trityl

Such ortho-lithiated tetrazole is either treated with an electrophile or with a metal halide M(L)n to give a transmetallated compound (M=Zn, Mg, Cu, B, Al or Cd). The latter is then treated with aryl halides in presence of catalyst (palladium or nickel) to yield biphenyl compounds of structure

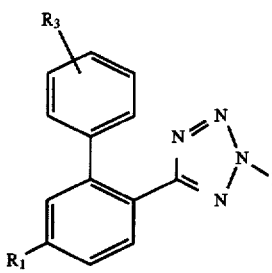

R¹ = H, t-butyl, phenoxy
R₂ = H or trityl
R₃ = alkyl, CH₂OH

In contrast, the process disclosed herein utilizes a Grignard reaction with, for example, a 1-(t-butyl)-3-(2-bromophenyl)tetrazole to produce the t-butylphenyltetrazole-2-magnesium bromide Grignard reagent rather than such ortho-lithiated reactant A which is then transmetallized with zinc chloride. The process disclosed herein therefore avoids the use of pyrophoric butyllithium.

Steps 3, 4 and 5 of Example 3 of the said U.S. Pat. No. 5,149,699 (American Home Product Corporation) discloses the preparation of the subject intermediate, {also known as 2,4-Dimethyl-5,6,8-trihydro-8-[[2'-(1-tert-butyl-1H-tetrazol-5-yl)[1,1-biphenyl]-4-yl]methyl]-7H-pyrido[2,3-d] pyrimidin-7-one,} by the following reaction sequence:

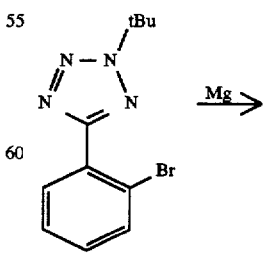

1

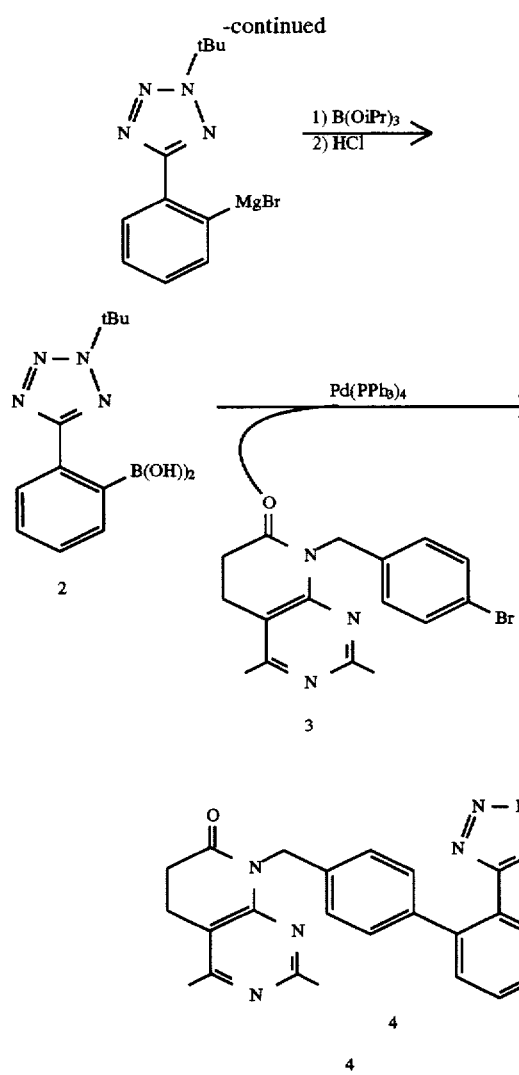

As seen from the above schematic, the 2-t-butyl-5-bromophenyl-2H-tetrazole, referred to hereinafter as "t-butylbromotetrazole", (1) is reacted with magnesium to produce the corresponding Grignard reagent which is then further reacted to produce the boronic acid (2). The overall yield for these step is 48%. The palladium catalyzed cross-coupling of the boronic acid (2) and the 8-[(4-bromophenyl)-methyl]5,8-dihydro-2,4-dimethyl-pyrido[2,3-d]pyrimidin-7(6H)-one, referred to hereinafter as "bromobenzyl lactam", (3) afford the subject intermediate in 66% yield. The process disclosed herein surprisingly provides better yields and avoids the isolation of the boronic acid (2).

Example 5 of the European patent EP 0550313A1 (Synthelabo) describes the preparation of the biphenyl product (5) by the following sequence.

R = H or OMe
$R_1$ = t-butyl, trityl

The aryl bromide (4) is converted to an organozinc which is used in the cross-coupling reaction to afford the biphenyl product (5) in yield ranging from 60 to 80%. In the process disclosed herein, the Grignard reagent is prepared from the aryltetrazole. This is an advantage since the arylhalide which does not contain the tetrazole ring can be fully functionalized.

Scheme IX of EP 0497150 A1 (American Cyanamid Company), shown below, shows a palladium or nickel catalyzed coupling of a 5-(2-M-phenyl)-1-(triphenylmethyl)-1H-tetrazole (108) with a 3-[4-($R^{40}$-phenyl)methyl]-quinazolinone (109); where M is selected from —MgBr, —Sn(loweralkyl of 1–4 carbon atoms or phenyl), Li or —Zn complex, and $R^{40}$ is selected from I, Br, or $OSO_2CF_3$. The only specific illustration of this reaction is in Example 90 where M is —MgBr and $R^{40}$ is bromo, that is, the tetrazole reactant is 5-(2-bromophenyl)-1-(triphenylmethyl)-1H-tetrazole, and the quinazolinone reactant is 3-[4-bromophenyl)methyl]-2-butyl-6-(1-methoxy-1-methylethyl)-4(3H)-quinazolinone].

Scheme IX
(EP 0 497 150 A1)

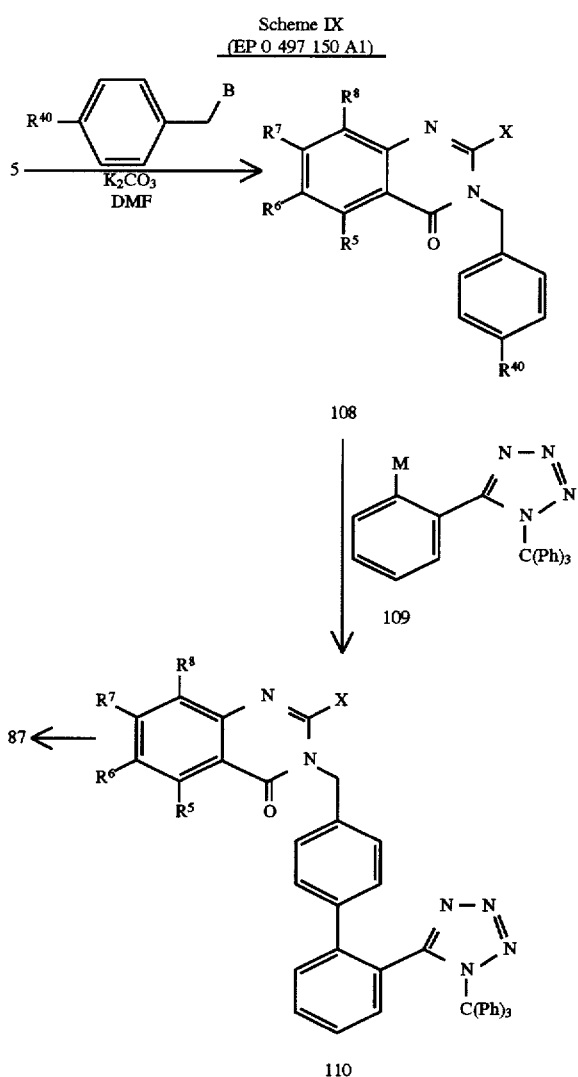

DETAILED DESCRIPTION OF THE INVENTION

According to the present invention there is provided a process for preparing a compound of the formula I:

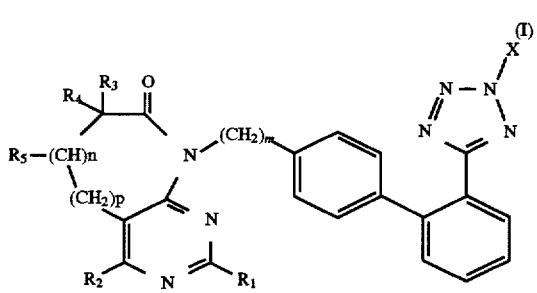

or a salt thereof;

wherein X is a protecting group and $R_1$, $R_2$, $R_3$ and $R_4$ are each independently hydrogen, $C_{1-6}$ alkyl or $C_{1-6}$ perfluoroalkyl, $R_5$ is hydrogen or, when n is 1, $R_5$ taken together with $R_3$ comprises a double bond; m is 1, 2 or 3; n is 0 or 1, and p is 0, 1 or 2;

by reacting a compound of the formula II:

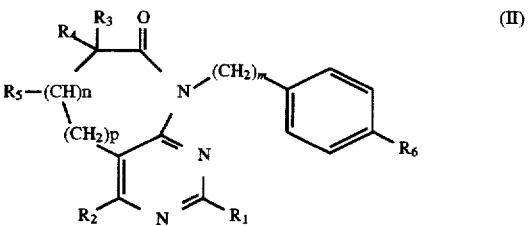

or a salt thereof;

wherein $R_1$ to $R_5$, m, n and p are each as defined above and $R_6$ is chloro, bromo, iodo or trifluoromethanesulfonyloxy; with a compound of the formula III:

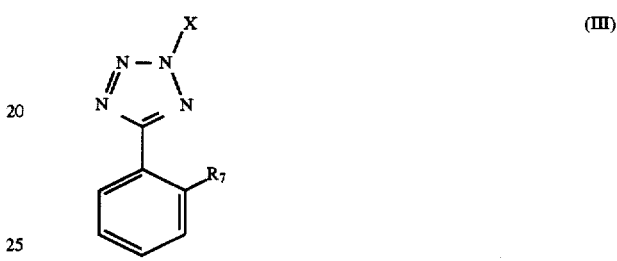

or a salt thereof;

wherein X is a protecting group and $R_7$ is a zinc or tin moiety (such as ZnCl, ZnBr or Sn($C_{1-6}$ alkyl)$_3$);

in the presence of a palladium or nickel catalyst.

The term 'protecting group' as used herein denotes a group which remains in position whilst a reaction (such as Grignard formation, transmetallization and/or coupling) is carried out, but can be readily removed thereafter, for example by acid or base hydrolysis. Common examples of protecting groups include tert-butyl, $C_{1-4}$ alkoxymethyl, methylthiomethyl, phenyl $C_{1-4}$ alkoxymethyl, p-methoxybenzyl, 2,4,6-trimethylbenzyl, 2-(trimethylsilyl) ethyl, tetrahydropyranyl and piperanyl. Further examples of protecting groups are given in the publication "Protecting Groups in Organic Synthesis" (Second Edition) by Greene & Wutz, published by John Wiley & Sons, Inc., 1991 (ISBN 0-471-62301-6) which is incorporated herein by reference.

Preferably X is a $C_{1-6}$ alkyl group or a phenyl or benzyl group, in each case optionally substituted by by one or more substituents selected from $C_{1-6}$ alkyl (eg methyl, ethyl, propyl, isopropyl, butyl, isobutyl, pentyl and hexyl), $C_{1-6}$ alkoxy (eg methoxy, ethoxy, propoxy, butoxy), nitro, amino, ($C_{1-6}$)alkylamino, di($C_{1-6}$)alkylamino, thio($C_{1-6}$)alkyl or phenyl substituents. Preferably X is a $C_{1-6}$ alkyl group optionally substituted by by one or more substituents selected from $C_{1-6}$ alkoxy (eg methoxy, ethoxy, propoxy, butoxy), nitro, amino, ($C_{1-6}$)alkylamino, di($C_{1-6}$)alkylamino or thio($C_{1-6}$)alkyl. Preferably X is a branched chain alkyl group such as tert-butyl.

Preferably in the process m is 1, n is 0, p is 1, $R_1$ and $R_2$ are each methyl and $R_3$ and $R_4$ are each hydrogen.

Preferably $R_6$ is bromo.

Preferably $R_8$ is MgBr.

Preferably $R_9$ is bromo.

Preferably the palladium or nickel catalyst is generated from a palladium or nickel salt, a reducing agent and a ligand or from a palladium or nickel salt and a species having dual reducing agent/ligand functions or from a palladium or nickel complex and a ligand.

Preferably the catalyst is generated from Pd(OAc)$_2$ or PdCl$_2$(PPh$_3$)$_2$, NiCl$_2$(dppe), NiCl$_2$(PPh$_3$)$_2$, Ni(acac)$_2$ or Pd$_2$(dba)$_3$ and one or more reducing agents/ligands selected from the group consisting of PPh$_3$, P(o-tolyl)$_3$, P(t-butyl)$_3$, P(2-furyl)$_3$, P(OiPr)$_3$, CuI, CuBr, AsPh$_3$, N$_2$H$_4$ and diisobutylaluminum hydride (DIBAL), 1,3-(diphenylphosphino)propane (DPPP or bis (1,4-diphenylphosphino)butane (DPPB).

Suitably the catalyst is generated in situ in the reaction vessel in which the reaction of the compounds of formulae II and III is carried out.

Preferably the reaction of the compounds of formulae II and III is carried out in the presence of a solvent species which is substantially immiscible with water, suitably a hydrocarbon solvent, and preferably an aromatic hydrocarbon solvent such as toluene or xylene.

Preferably the reaction of the compounds of formulae II and III is carried out in the presence of a mixture of solvent species which includes a solvent species which is substantially immiscible with water and a solvent species in the form of an ether. Preferably the ratio of the solvent species which is substantially immiscible with water to the solvent species in the form of an ether is from 5:1 to 1:5. Preferably the solvent species in the form of an ether is tetrahydrofuran (THF).

Preferably the compound of formula III is prepared by transmetallizing a compound of formula IV

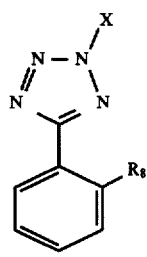

(IV)

or a salt thereof, wherein X is a protecting group and R$_8$ is MgBr or MgI; with a transmetallizing agent selected from zinc chloride, zinc bromide, tri(C$_{1-6}$alkyl)tin chloride or tri(C$_{1-6}$alkyl)tin bromide. Preferably zinc chloride is used as the transmetallizing agent.

Preferably the reaction of the compound of formula IV with the transmetallizing agent is carried out in the presence of a solvent species which is substantially immiscible with water such as a hydrocarbon solvent, preferably an aromatic hydrocarbon solvent such as toluene or xylene. Typically the solvent which is substantially immiscible with water will have a low polarity, and may be substantially non-polar.

Preferably the reaction of the compound of formula IV with the transmetallizing agent is carried out in the presence of a mixture of solvent species which includes a solvent species which is substantially immiscible with water and a solvent species in the form of an ether, such as tetrahydrofuran (THF). Preferably the volume ratio of the solvent species which is substantially immiscible with water to the solvent species in the form of an ether is from 5:1 to 1:5, preferably from 5:1 to 1:1.

Preferably the reaction of the compound of formulae IV and in situ generation of the palladium or nickel catalyst are carried out substantially in the same reaction vessel. Preferably the reactions of the compounds of formulae II, III and IV and in situ generation of the palladium or nickel catalyst are carried out substantially in the same reaction vessel.

Preferably the compound of formula IV is prepared by reacting a compound of formula V:

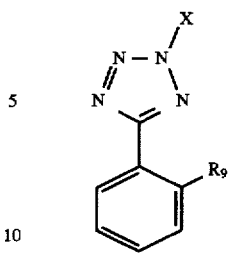

(V)

or a salt thereof;

wherein X is a protecting group and R$_9$ is Br or I; with magnesium.

Preferably the reaction of the compound of formula V with magnesium is carried out in the presence of a solvent in the form of an ether such as THF, dimethoxyethane (DME), diethylether or 1,4-dioxan, of which THF is preferred.

Suitably at least a portion of the ether solvent present during the reaction of the compound of formula V with magnesium is retained during the reaction of the compound of formula IV with the transmetallizing agent and suitably at least a portion of the ether solvent present during the reaction of the compound of formula V with magnesium is retained during the reaction of the compounds of formula II and III.

Suitably the process comprises the further step of deprotecting the compound of formula I to provide a compound of formula VI:

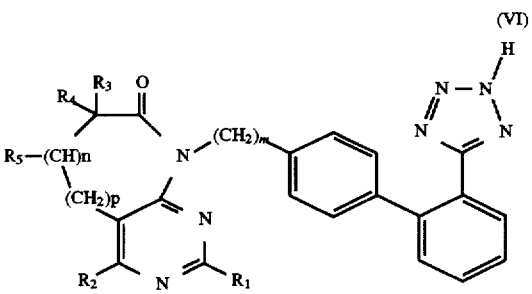

(VI)

or a salt thereof;

wherein R$_1$, R$_2$, R$_3$ and R$_4$ are each independently hydrogen, C$_{1-6}$alkyl or C$_{1-6}$perfluoroalkyl, R$_5$ is hydrogen or, when n is 1, R$_5$ taken together with R$_3$ comprises a double bond; m is 1, 2 or 3; n is 0 or 1, and p is 0, 1 or 2.

In a preferred form the invention provides a process for producing 8-[2'-(2(1)-tert-butyl-2H-tetrazol-5-yl)-biphenyl-4-yl-methyl]-2,4-dimethyl-5,8-dihydro-6H-pyrido[2,3-d]pyrimidin-7-one (or such a compound wherein a benzyl or p-methoxybenzyl group is present in place of the tert-butyl group) or a salt thereof, said process characterized in (A) reacting 2-tert-butyl-5-(2-bromo- or iodophenyl)-2H-tetrazole with magnesium to yield the bromo or iodo [2-[2-(tert-butyl)-2H-tetrazol-5-yl]phenyl]magnesium Grignard reagent, (B) transmetallizing said Grignard reagent with zinc chloride, zinc bromide or tributyltin chloride; and (C) reacting the transmetallized product with 8-[(4-bromo-, iodo- or trifluoromethanesulfonyloxyphenyl)-methyl]5,8-dihydro-2,4-dimethyl-pyrido[2,3-d]pyrimidin-7(6H)-one in the presence of a palladium or nickel catalyst to yield the product;

(wherein throughout the process a benzyl or p-methoxybenzyl group may be present in place of the tert-butyl group).

Preferably 2-tert-butyl-5-(2-bromophenyl)-2H-tetrazole is used in step A.

Preferably zinc chloride is the transmetallizing agent in step C.

Preferably 8-[(4-bromophenyl)-methyl]-5,8-dihydro-2,4-dimethyl-pyrido[2,3-d]-pyrimidin-7(6H)-one is reacted with chloro or bromo[2-[2-(tert-butyl)-2H-tetrazol-5-yl]phenyl] zinc in step C. Preferably the Grignard reagent is prepared by reacting 2-tert-butyl-5-(2-bromophenyl)-2H-tetrazole with magnesium.

Preferably a palladium catalyst is used in step C.

Preferably the palladium catalyst is generated from $PdCl_2$, $Pd(OAc)_2$, $Pd_2(dba)_3$, or $PdCl_2(PPh_3)_2$ and an additive selected from the group consisting of $PPh_3$, $P(o-tolyl)_3$, $P(2-furyl)_3$, $P(t-butyl)_3$, $P(OiPr)_3$, CuI, CuBr, $AsPh_3$, DPPP, DPPB and DIBAL.

Preferably a palladium catalyst is generated in the reaction vessel containing the chloro or bromo[2-[2-(tert-butyl)-2H-tetrazol-5-yl]phenyl]zinc.

Preferably the reactions of steps B and C and the generation of the palladium or nickel catalyst are carried out in the same reaction vessel.

In a further preferred embodiment the invention provides a method for producing 8-[2'-(2(1)-tert-butyl-2H-tetrazol-5-yl)-biphenyl-4-yl-methyl]-2,4-dimethyl-5,8-dihydro-6H-pyrido[2,3-d]pyrimidin-7-one (or such a compound wherein a benzyl or p-methoxybenzyl group is present in place of the tert-butyl group) or a salt thereof, said process characterized in:

(B) transmetallizing bromo[2-[2-(tert-butyl)-2H-tetrazol-5-yl]phenyl]magnesium Grignard reagent with zinc chloride; and (C) reacting the transmetallized product with 8-[(4-bromophenyl)-methyl]-5,8-dihydro-2,4-dimethyl-pyrido[2,3-d]pyrimidin-7(6H)-one in the presence of a palladium catalyst to yield the product;

(wherein throughout the process a benzyl or p-methoxybenzyl group may be present in place of the tert-butyl group).

Preferably the process comprises the further step of deprotecting the product to provide 8-[2'-(1H-tetrazol-5-yl)-biphenyl-4-yl-methyl]-2,4-dimethyl-5,8-dihydro-6H-pyrido[2,3-d]pyrimidin-7-one or a salt thereof.

In a further aspect the invention provides compound of the formula VII:

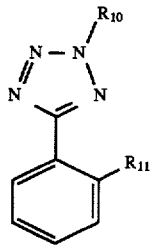

(VII)

or a salt thereof;

wherein $R_{10}$ is a $C_{1-6}$ alkyl group and $R_{11}$ is a zinc moiety such as ZnCl or ZnBr.

Preferably $R_{10}$ is a branched chain alkyl group such as tert-butyl.

A preferred process of the invention for production of the intermediate 8-[2'(2(1)-tert-butyl-2H-tetrazol-5-yl)-biphenyl-4-yl-methyl]-2,4-dimethyl-5,8dihydro-6H-pyrido [2,3-d]pyrimidin-7-one is shown in the following schematic diagram.

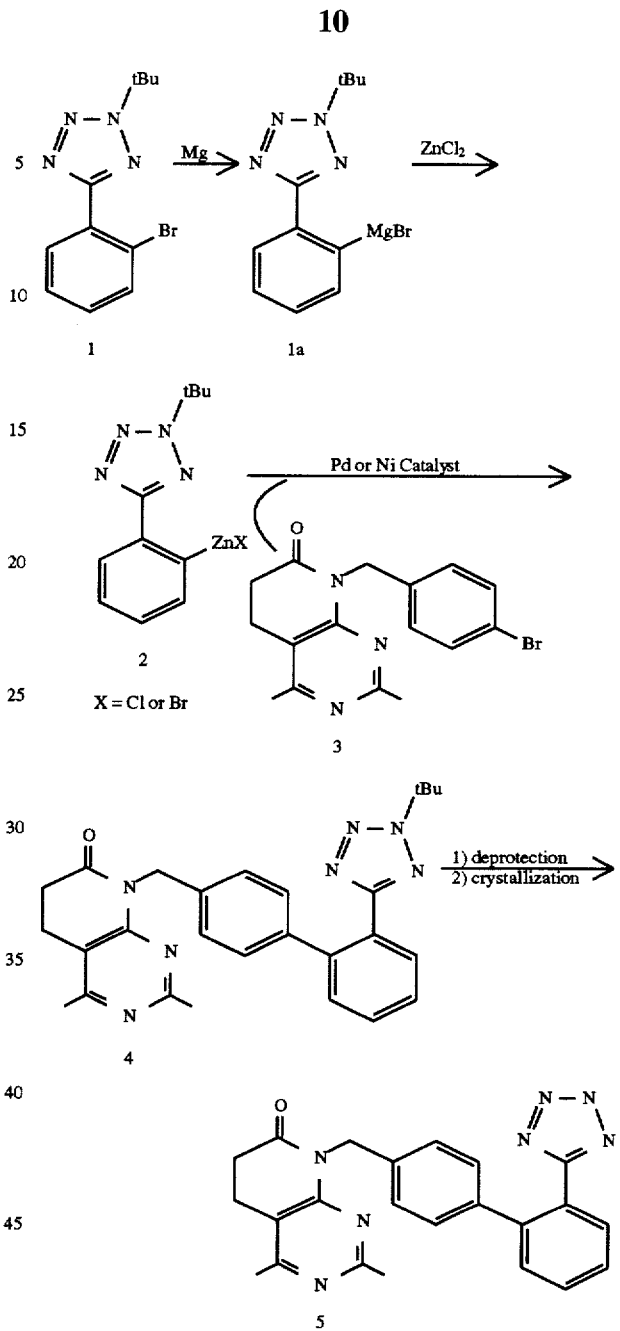

The t-butylbromotetrazole (1) reacts with magnesium to produce the corresponding Grignard reagent (1a) which is treated with zinc chloride to afford the organozinc (2). The latter is not isolated and is treated with the bromobenzyl lactam (3) in presence of catalytic amount of palladium or nickel catalyst to produce the desired intermediate (4). Deprotection by known means (for example by acid catalysed hydrolysis, eg using 2N HCl) and further crystallization, as necessary, yields the desired drug substance product (5). Suitable means of deprotection are described in U.S. Pat. No. 5,149,699 to Ellingboe et al. (see eg Example 3, step 6; which is herein incorporated by reference) and in J. W. Ellingboe et al., J. Med. Chem. 1994, 37, 542–550. For example, the protected compound may be mixed with an approximately ten molar excess of methanesulphonic acid in toluene and heated under reflux for about 18 hours. The mixture may then be concentrated and water and 1N KOH may be added to give a solution of pH 8. The resulting mixture may be extracted with ethyl acetate to remove unreacted starting material, and the aqueous phase may be acidified with 1N HCl to pH 5. The product may then be extracted into ethyl acetate and dried over MgSO$_4$ and concentrated and, if necessary triturated (eg with acetone/ether) to give the deprotected product as a solid.

Particularly preferred is a process for producing 8-[2'-(2(1)-tert-butyl-2H-tetrazol-5-yl)-biphenyl-4-yl-methyl]-2,4-dimethyl-5,8-dihydro-6H-pyrido[2,3-d]pyrimidin-7-one or a salt thereof, said process characterized in (A) reacting 2-tert-butyl-5-(2-bromophenyl)-2H-tetrazole with magnesium to yield the bromo[2-[2-(tert-butyl)-2H-tetrazol-5-yl]phenyl]magnesium Grignard reagent, (B) transmetallizing said Grignard reagent with zinc chloride to produce bromo[2-[2-(tert-butyl)-2H-tetrazol-5-yl]phenyl]zinc, and (C) reacting said chloro[2-[2-(tert-butyl)-2H-tetrazol-5-yl]phenyl]zinc with 8-[(4-bromophenyl)-methyl]5,8-dihydro-2,4-dimethyl-pyrido[2,3-d]pyrimidin-7(6H-one in the presence of a palladium catalyst to yield the product 8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one or a salt thereof.

In the above reactions, the t-butylbromotetrazole (1) [or other compound of formula III] is preferably prepared and used in a molar excess of the bromobenzyl lactam (3) [or other compound of formula II] of 1–2 to 1, preferably 1.1–1.4 to 1, and most preferably 1.2–1.3 to 1. The transmetallization agent is preferably used in a 1–3 to 1 molar ratio, preferably in a 1.5–3 to 1 molar ratio, most preferably in a 2–2.5 to 1 molar ratio to the amount of t-butylbromotetrazole (1) [or other compound of formula III]. The palladium or nickel catalyst is preferably used in a 0.005–0.05 to 1 molar ratio, preferably in a 0.01–0.03 to 1 molar ratio, and most preferably in a 0.015–0.030 to 1 molar ratio to the bromobenzyl lactam (3) [or other compound of formula II].

The solvent used in Step A (or more generally in reaction of compounds of formula V) is an ether, such as tetrahydrofuran (THF), dimethoxyethane (DME), diethyl ether, or dioxane, which may be used in Steps B and C (or more generally in reaction of compounds of formula II, III and IV). The preferred solvent in Step A (or more generally in reaction of compounds of formula V) is THF. Preferably an additional solvent (in addition to a main solvent) is added in step B (or more generally in reaction of compounds of formula IV), which additional solvent is preferably a a water immiscible solvent. The additional solvent is preferably present in a volume ratio of 0.1–5 to 1, preferably 0.3–4 to 1, most preferably 1–2 to 1, relative to the main solvent. Preferably, the additional solvent is miscible with the main solvent but immiscible with water. The additional solvent is preferably hydrocarbon and more preferably an aromatic hydrocarbon solvent is preferred. A substituted phenyl or benzyl solvent, such as, toluene or xylene, is particularly preferred.

Preferably in the transmetallization step B (or more generally in reaction of compounds of formula IV) the temperature is kept low in order to prevent reaction between the solvent and the transmetallizing agent, but sufficiently high to ensure that the reagents remain in solution. A suitable temperature range is 30° to 50° C., preferably 30° to 40° C. The preferred temperatures for the cross-coupling step C are 50°–70° C., and more preferably about 60°–65° C.

Steps B and C (or more generally reaction of compounds of formula II, III and IV) are preferably run in one reaction vessel without isolation of the transmetallization product of Step B (or more generally the compound of formula III). Preferably, the generation of the catalyst is also carried out in the same rection vessel used for steps B and C (or more generally in reaction of compounds of formula II, III and IV).

Preferably in the palladium or nickel catalyst the palladium or nickel is in the zero oxidation state. The palladium or nickel catalyst may either be added pre-formed or may be generated in situ. Suitable pre-formed palladium and nickel catalysts for step C include Pd$_2$dba$_3$, Ni(PPh$_3$)$_4$, and Pd(PPh$_3$)$_4$. Alternatively, the catalyst can be generated in situ by mixing Pd(OAc)$_2$, PdCl$_2$, PdCl$_2$(PPh$_3$)$_2$, NiCl2 (dppe), NiCl$_2$(PPh$_3$)$_2$, Ni(acac)$_2$ or Pd$_2$dba$_3$ with one or more ligand/reducing agents as additives, such as, PPh$_3$, P(o-tolyl)$_3$, P(t-butyl)$_3$, P(2-furyl)$_3$, P(OiPr)$_3$, CuI, CuBr, AsPh$_3$, DIBAL, dppp or dppb. A particularly preferred in situ catalyst is generated by adding Pd(OAc)$_2$ and PPh$_3$. [acac=acetonylacetone; dba=dibenzylidene acetone; DIBAL=diisobutylaluminum hydride; dppp=1,3-(diphenylphosphino)propane; and dppb=bis(1,4-diphenylphosphino)butane.]

The Following Examples Further Illustrate the Practice of the Invention

EXAMPLE 1

Preparation of 8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one (i) Organozinc preparation=Chloro[2-[2-(tert-butyl)-2H-tetrazol-5-yl]phenyl]zinc 640 g of t-butylbromotetrazole (1) was dissolved in 1080 g tetrahydrofuran. 10% of this t-butylbromotetrazole solution was added to a stirred suspension of 75.6 g magnesium (1.37 eq.) in 1080 g tetrahydrofuran at 40° C. 10.9 g 1,2-dibromoethane was added and the reaction mixture was stirred for one hour at 40° C. The remainder of the t-butylbromotetrazole solution was added to the magnesium suspension at a steady rate over 5 hours while adding 10 portions of 10.9 g 1,2-dibromoethane every hour. The reaction mixture was then stirred for 20 hours at 40° C. 424 g of zinc chloride (1.37 eq.) in 2020 g tetrahydrofuran was the added to the resulting Grignard reagent while maintaining the temperature 25°–35° C. The resulting suspension was stirred at 30° C. for one hour.

(ii) Catalyst preparation—54.1 g of 25% DIBAL toluene solution was added to a suspension of 30.6 g bis (triphenylphosphine)palladium (II) chloride in 620 g tetrahydrofuran at 30° C. The resulting black solution was stirred for one hour at 30° C.

(iii) Cross-coupling—8-[2'(2(1)-tert-butyl-2H-tetrazol-5-yl)-biphenyl-4-yl-methyl]-2

603.4 g bromobenzyl lactam (3) (0.77 eq. of (1)) was added to the organozinc suspension, followed by addition of the catalyst solution. The resulting suspension reaction mixture was heated for 20 hours at 64° C. Thereafter, the reaction mixture was cooled to 0° C. and 2.1 liter HCl and 1214 g toluene were added to it while maintaining the temperature 0°–10° C. The resulting mixture was stirred for 30 minutes and the layers separated. The organic layer was washed with 350 ml 1N HCl. The layers were separated and 765 g concentrated ammonium hydroxide were added to this while maintaining the temperature 0°–10° C. The resulting layers layers were and 1821 g toluene was added to the organic layer and then 2.1 l 2N HCl. The resulting mixture was stirred for 30 minutes at 5° C. The resulting layers were separated and the organic layer was washed with 3×0.7 L 2N HCl. All of the 2N HCl layers were combined and stirred with 303 g toluene. The layers layers were separated and 2428 g toluene were added to the aqueous layer, followed by 2.8 l concentrated ammonium hydroxide to the organic phase while maintaining the temperature 0°–10° C. The layers were separated and the aqueous layer washed with 607 g toluene. The two organic layers were combined and washed with 2×350 ml water. The organic layer was dried over sodium sulfate and concentrated to an oil. 637 g of product, yield—78% of crude product.

EXAMPLE 2

Preparation of 8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one (i) Organozinc preparation=Chloro[2-[2-(tert-butyl)-2H-tetrazol-5-yl]phenyl]zinc 40 g of t-butylbromotetrazole (1) were dissolved in 35.6 g tetrahydrofuran. 10% of this solution was added to a stirred suspension of 4.8 g magnesium in 35.6 g tetrahydrofuran at 50° C. 2.4 g 1,2-dibromoethane were added to this solution which was them stirred 30 minutes at 50° C. The remainder of the butylbromotetrazole solution was then added to the magnesium suspension at a steady rate over 4 hours at 50° C. and then stirred for 2 hours at 50° C. Thereafter, 0.4 g 1,2-dibromoethane were added and stirred at 50° C. for another 5 hours. Half the resulting Grignard reagent was transferred to a flask containing a solution of 10.2 g zinc chloride in 43 g tetrahydrofuran and the entire solution stirred for 1.5 hours at 35° C.

(ii) Catalyst preparation 2.5 mL of 25% DIBAL toluene solution was added to a suspension of 0.476 g triphenylphosphine and 1.27 g bis(triphenylphosphine)palladium (II) chloride in 21 g tetrahydrofuran at 25° C. Stir 1.5 hours at 25° C.

(iii) Cross-coupling=8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one 20.9 g of bromobenzyl lactam (3) was added to the organozinc suspension and then the catalyst. The resulting mixture was heated to 70° C. for 2.5 hours and then cooled to 0°–5° C. 60 ml of 13% aqueous acetic acid and 28 g toluene were added. The resulting mixture was stirred and the layers were separated. 34.7 g toluene and 10 ml 13% aqueous acetic acid were added to the organic layer and the mixture was stirred. The layers were separated and the organic layer was washed with 10 ml 13% aqueous acetic acid. The layers were separated again and 36 ml concentrated ammonium hydroxide was added. The layers were stirred and separated again. 17 g toluene and 60 ml 2N HCl was added to the organic layer. The resulting mixture was stirred for 30 minutes at 10° C., the layers were then separated and the organic was washed with 2×20 ml 2N HCl. The 2N HCl layers were combined and washed with 9 g toluene. The layers were separated and 69.4 g toluene was added to the aqueous and then 30 mL NH₄OH while maintaining the temperature at 0°–10° C. The layers were separated and the aqueous layer was washed with 17 g toluene. The two organic layers were combined and washed with 2×10 ml water and dried over sodium sulfate and concentrated. 10 g isopropanol was added and the resulting mixture was heated to 50° C. 17.8 g heptane was added and the resulting mixture was cooled to 25° C. and then stirred 16 hours at 25° C. and then 2 hours at 0° C. The resulting mixture was filtered and the crystal was washed with 2×15 ml of a 2/1 heptane/isopropanol mixture to give 19.9 g [based on (3)]yield=70% of crystallized product.

EXAMPLE 3

Preparation of 8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one (i) Grignard reagent preparation=Bromo[2-[2-(tert-butyl)-2H-tetrazol-5-yl]phenyl]magnesium 600 g of t-butylbromotetrazole (1) were dissolved in 640 g tetrahydrofuran. 10% of this t-butylbromotetrazole solution was added to a stirred suspension of 72.6 g magnesium in 320 g tetrahydrofuran at 50° C. Add 3.27 g of 1,2-dibromoethane was added to this solution which was then stirred for 30 minutes at 50° C. The remainder of the t-butylbromotetrazole solution was then added to this magnesium suspension at a steady rate over 6 hours, followed by stirring 2 hours at 50° C. A further 3.27 g of 1,2-dibromoethane was added to this solution, followed by stirring at 50° C. for another 5 hours. Cool to 25° C.

(ii) Catalyst preparation—38.61 g of triphenyl phosphine were dissolved in 291 g tetrahydrofuran. 11.01 g palladium acetate were added to this solution and the resulting suspension was heated at 60° C. for 3 hours and then cooled to 25° C.

(iii) Organozinc preparation (in situ) and Cross-coupling—8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one.

565.2 g of zinc chloride (2) and 567.3 of bromobenzyl lactam (3) were dissolved in 1640 g of tetrahydrofuran. The catalyst was added and the resulting mixture was heated to 60° C. The Grignard reagent was then added to the mixture over a period of 8 hours while maintaining the temperature at 60° C. When the addition was completed, the reaction mixture was maintained at 60° C. for an additional 4 hours and then cooled to 25° C. The cooled reaction mixture was poured into 1800 g of 10% aqueous acetic acid and 520 g toluene. The layers were separated and 1040 g of toluene and 300 g of water were added to the organic layer. The layers were separated and the organic layer was sequentially washed with 300 g of water, 675 g ammonium hydroxide and 300 g of water. 520 g of toluene and 1800 ml, 2N aqueous hydrochloride acid were then added to the organic layer, which was then stirred at 10° C. for 1 hour. The layers were separated and the organic layer extracted with 2×600 ml of 2N aqueous hydrochloric acid. The 2N aqueous hydrochloric acid extracts were combined and washed with 260 g of toluene. 2081 g of toluene were added to the acidic aqueous mixture and then 648 g of ammonium hydroxide. The resulting layers were separated and the organic layer washed with 2×300 g of water. The resulting organic layer was concentrated to an oil, to which 312 g of isopropanol were added and the resulting mixture was heated to 50° C. 543 g of heptane were added to this mixture, followed by cooling to 0° C. and then filtering. 581 g [based on (3)], yield 76% of crystallized product. 581 g [based on (3)]

EXAMPLE 4

Preparation of 8-[2'(2(1)-tert-butyl-2H-tetrazol-5-yl)-biphenyl-4-yl-methyl]-2,4-dimethyl-5,8-diydro-6H-pyrido[2,3-d]pyrimidin-7-one 600 g of t-butylbromotetrazole (1) was dissolved in 640 g tetrahydrofuran. 10% of this t-butylbromotetrazole solution was added to a stirred suspension of 72.6 g magnesium in 320 g tetrahydrofuran at 50° C. 3.27 g of 1,2-dibromoethane was added to the resulting mixture and the mixture was stirred 30 minutes at 50° C. The remainder of the t-butylbromotetrazole solution was added to the magnesium suspension at a steady rate over 6 hours. The resulting mixture was stirred a further 2 hours at 50° C., 3.27 g of 1,2-dibromoethane was added and stirring was continued at 50° C. for another 5 hours. The resulting Grignard reagent mixture was cooled to 25° C. 527.2 g of zinc chloride was then dissolved in a mixture of 844 g toluene and 844 g of tetrahydrofuran. The Grignard reagent was added to the zinc chloride solution and the resulting suspension stirred for 15 minutes at 25° C. to provide an organozinc mixture.

527.2 g of bromobenzyl lactam (3) 10.13 g of palladium acetate and 23.7 g of triphenyl phosphine were added to the organozinc mixture sequentially. The resulting reaction mixture was kept at 60° C. for 12 hours. Thereafter the mixture was cooled to 25° C., 733 g of water added and the layers then separated. The aqueous layer was washed with 200 g of toluene and the resulting organic layer was combined with the first organic layer. The resulting mixture was washed with 3×733 g of water, 232 g of ammonium hydroxide and 533 g of water. The organic layer was concentrated to an oil, 1433 g of isopropanol added and The resulting mixture heated to 50° C. The mixture was cooled to −10° C. and filtered. 491 g [based on (3)], yield=69% of crystallized product.

EXAMPLES 5–8

Preparation of 8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one (i) Grignard reagent preparation—A solution of t-butylbromotetrazole (3.4 g; 0.01 moles) and 1,2-dibromoethane (0.4 g; 0.002 moles) was added at 25° C. to a stirred mixture of magnesium (5.5 g; 0.23 moles) and THF (26 ml) allowing the temperature to rise up to about 55° C.; the mixture was kept under stirring at 55° C. for 30 minutes, then THF (40 ml) was added. A second portion of t-butylbromotetrazole (30.4 g; 0.1 moles) was added dropwise during 4.5 hours. At the end of the addition, the mixture was kept at 55° C. for 17 hours.

(ii) Transmetallization—The Grignard solution was transferred in a dropping funnel and added in about 15 minutes to a stirred mixture of ZnCl$_2$ (30 g; 0.22 moles) and toluene (117 ml) at 25° C., while cooling the reaction mixture to keep the temperature below 45° C. At the end of the addition, the mixture was stirred for 30 minutes.

(iii) Catalyst preparation (in situ) and cross-coupling (in situ)—To the organozinc mixture, bromobenzyl lactam (30 g; 0.086 moles) and Pd(OAc)$_2$ (0.29 g; 0.0013 moles) were added sequentially. The reaction was warmed up to 60° C. and Ph$_3$P (0.34 g; 0.0013 moles) was added. After 5 minutes the phosphine (see Table 1) was added. The mixture was maintained at 60° C. for 21 hours.

The mixture was cooled to 25°–30° C. and added with water (40 g) and acetic acid (4.1 g). The organic phase was separated and washed with water (40 g). The organic phase was added with water (10 g) and 30% ammonium hydroxide (9.3 g); after separation of the phases, the organic layer was added with water (30 g) and acetic acid (about 1.66 g) until pH 5. The organic phase was separated and analysed by HPLC against an external standard (see Table 1).

The following examples were carried out according to the method described in example 5 substituting the phosphine with the additives (i.e. dppp, etc.) reported in Table 1. Yields were calculated against changed bromobenzyl lactam.

TABLE 1

| Ex. No. | Phosphine | mmoles | Time (hours) | Yield |
| --- | --- | --- | --- | --- |
| 5 | dppp[1] | 1.3 | 21 | 70.3% |
| 6 | dppb[2] | 1.3 | 21 | 80.4% |
| 7 | (2-furyl)$_3$P | 2.6 | 21 | 66.3% |
| 8 | (2-tolyl)$_3$P | 2.6 | 21 | 78.2% |

[1]dppp = 1,3-(diphenylphosphino)propane
[2]dppb = bis(1,4-diphenylphosphino)butane

EXAMPLE 9

Preparation of 8-[2'(2(1)-tert-butyl-2H-tetrazol-5-yl)-biphenyl-4-yl-methyl]-2,4-dimethyl-5,8-dihydro-6H-pyrido[2,3-d]pyrimidin-7-one (i) Grignard reagent preparation—A solution of t-butylbromotetrazole (1) (3.4 g; 0.011 moles) and 1,2-dibromoethane (0.4 g; 0.002 moles) was added at 25° C. to a stirred mixture of magnesium (3.9 g; 0.16 moles) and THF (26 ml) allowing the temperature to rise up to about 55° C.; the mixture was kept under stirring at 55° C. for 30 minutes, then THF (40 ml) was added. A second portion of t-butylbromotetrazole (1) (30.4 g; 0.1 moles) was added dropwise during 4.5 hours. At the end of the addition, the mixture was kept at 55° C. for 17 hours.

(ii) Transmetallization—The Grignard solution was transferred in a dropping funnel and added in about 15 minutes to a stirred mixture of ZnCl$_2$ (30 g; 0.22 moles) and toluene (117 ml) at 25° C., while cooling the reaction mixture to keep the temperature below 45° C. At the end of the addition, the reaction was warmed up to 45°–50° C. and stirred for 1 hour.

(iii) Catalyst preparation (in situ) and cross-coupling (in situ)—To the organozinc mixture, bromobenzyl lactam (3) (30 g; 0.086 moles) and Pd(OAc)$_2$ (0.29 g; 0.0013 moles) were added sequentially. The reaction was warmed up to 60° C. and Ph$_3$P (1.02 g; 0.039 moles) was added. The mixture was kept at 60° C. for 20 hours.

The mixture was cooled to 25°–30° C. and added with water (40 g) and acetic acid (4.2 g). The organic phase was separated and washed with water (40 g). The organic phase was added with water (10 g) and 30% ammonium hydroxide (9.3 g), separated and added again with water (30 g) and acetic acid (1.7 g) until pH5. The organic phase was separated and evaporated at 60° C. under vacuum to give a residue which was dissolved in isopropyl alcohol (85 g) at 50° C. The solution was allowed to crystallize by slow cooling to −10° C. and kept at this temperature overnight. The product was collected by filtration, washed with isopropyl alcohol and dried at 60° C. under vacuum to yield 30 g of pure product (74.6% yield based on compound 3).

We claim:

1. A process for preparing a compound of the formula I:

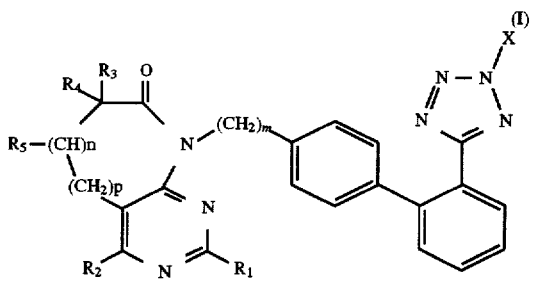

or a salt thereof;
wherein X is a protecting group and $R_1$, $R_2$, $R_3$ and $R_4$ are each independently hydrogen, $C_{1-6}$ alkyl or $C_{1-6}$ perfluoroalkyl, $R_5$ is hydrogen or, when n is 1, $R_5$ taken together with $R_3$ comprises a double bond; m is 1, 2 or 3; n is 0 or 1, and p is 0, 1 or 2;
by reacting a compound of the formula II:

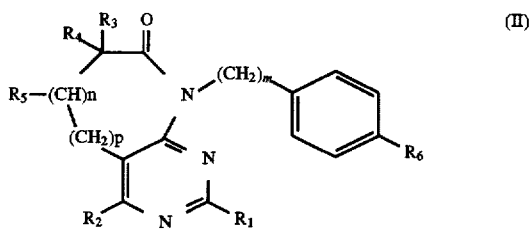

or a salt thereof;
wherein $R_1$ to $R_5$, m, n and p are each as defined above and $R_6$ is chloro, bromo, or iodo;
with a compound of the formula III:

or a salt thereof;
wherein X is a protecting group and $R_7$ is a zinc halide; in the presence of a palladium or nickel catalyst.

2. A process as claimed in claim 1 wherein the palladium or nickel catalyst is generated from a palladium or nickel salt, a reducing agent and a ligand or from a palladium or nickel salt and a species having dual reducing agent/ligand functions.

3. A process as claimed in claim 2 wherein the catalyst is generated from $Pd(OAc)_2$ or $PdCl_2(PPh_3)_2$ NiCl2(dppe), $NiCl_2(PPh_3)_2$, $Ni(acac)_2$ or $Pd_2dba_3$ and one or more reducing agents/ligands selected from the group consisting of $PPh_3$, $P(o\text{-tolyl})_3$, $P(2\text{-furyl})_3$, $P(t\text{-butyl})_3$, $P(OiPr)_3$, CuI, CuBr, $AsPh_3$ and diisobutylaluminum hydride (DIBAL), 1,3-bis-diphenylphosphine-propane (DPPP) or 1,3-bis-diphenylphosphine-butane (DPPB).

4. A process as claimed in claim 1 wherein the catalyst is generated in situ in the reaction vessel in which the reaction of the compounds of formulae II and III is carried out.

5. A process as claimed in claim 1 wherein the reaction of the compounds of formulae II and III is carried out in the presence of a solvent species which is substantially immiscible with water.

6. A process as claimed in claim 5 wherein the solvent species which is substantially immiscible with water is a hydrocarbon solvent.

7. A process as claimed in claim 6 wherein the hydrocarbon solvent is an aromatic hydrocarbon solvent.

8. A process as claimed in claim 7 wherein the aromatic hydrocarbon solvent is toluene or xylene.

9. A process as claimed in claim 1 wherein the reaction of the compounds of formulae II and III is carried out in the presence of a mixture of solvent species which includes a solvent species which is substantially immiscible with water and a solvent species in the form of an ether.

10. A process as claimed in claim 9 wherein the ratio of the solvent species which is substantially immiscible with water to the solvent species in the form of an ether is from 5:1 to 1:5.

11. A process as claimed in claim 9 wherein the solvent species in the form of an ether is tetrahydrofuran (THF).

12. A process as claimed in claim 1 wherein the compound of formula III is prepared by transmetallizing a compound of formula IV

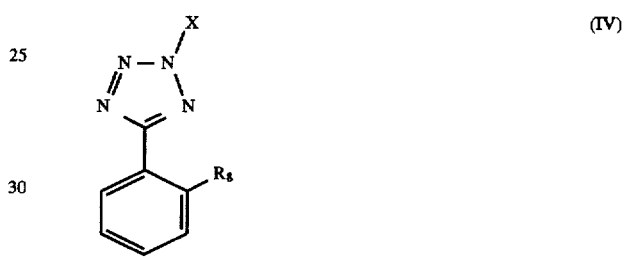

or a salt thereof;
wherein X is a protecting group and $R_8$ is MgBr or MgI; with a transmetallizing agent selected from zinc chloride or zinc bromide.

13. A process as claimed in claim 12 wherein zinc chloride is used as the transmetallizing agent.

14. A process as claimed in claim 12 wherein the reaction of the compound of formula IV with the transmetallizing agent is carried out in the presence of a solvent species which is substantially immiscible with water.

15. A process as claimed in claim 14 wherein the solvent species which is substantially immiscible with water is a hydrocarbon solvent.

16. A process as claimed in claim 15 wherein the hydrocarbon solvent is an aromatic hydrocarbon solvent.

17. A process as claimed in claim 16 wherein the aromatic hydrocarbon solvent is toluene or xylene.

18. A process as claimed in claim 12 wherein the reaction of the compound IV with the transmetallizing agent is carried out in the presence of a mixture of solvent species which includes a solvent species which is substantially immiscible with water and a solvent species in the form of an ether.

19. A process as claimed in claim 18 wherein the volume ratio of the solvent species which is substantially immiscible with water to the solvent species in the form of an ether is from 5:1 to 1:5, preferably from 5:1 to 1:1.

20. A process as claimed in claim 18 wherein the solvent in the form of an ether is tetrahydrofuran (THF).

21. A process as claimed in claim 12 wherein the compound of formula IV is prepared by reacting a compound of formula V:

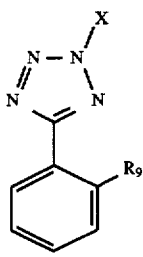

(V)

or a salt thereof;
wherein X is a protecting group and $R_9$ is Br or I;
with magnesium.

22. A process as claimed in claim 21 wherein the reaction of the compound of formula V with magnesium is carried out in the presence of a solvent in the form of an ether.

23. A process as claimed in claim 22 wherein at least a portion of the ether solvent present during the reaction of the compound of formula V with magnesium is retained during the reaction of the compound of formula IV with the transmetallizing agent.

24. A process as claimed in claim 23 wherein at least a portion of the ether solvent present during the reaction of the compound of formula V with magnesium is retained during the reaction of the compounds of formula II and III.

25. A process as claimed in claims 21 wherein the reactions of the compounds of formulae IV and V and in situ generation of the palladium or nickel catalyst are carried out substantially in the same reaction vessel.

26. A process as claimed in claim 25 wherein the reactions of the compounds of formulae II, III IV and V and in situ generation of the palladium or nickel catalyst are carried out substantially in the same reaction vessel.

27. A process as claimed in claim 1 comprising the further step of deprotecting the compound of formula I to provide a compound of formula VI:

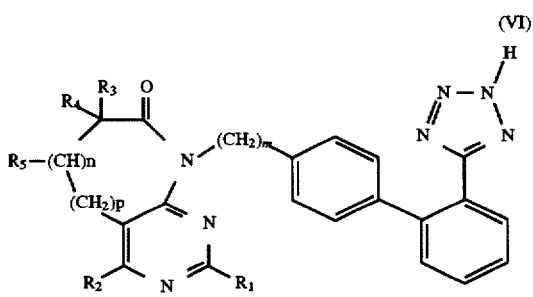

(VI)

or a salt thereof;
wherein $R_1$, $R_2$, $R_3$ and $R_4$ are each independently hydrogen, $C_{1-6}$ alkyl or $C_{1-6}$ perfluoroalkyl, $R_5$ is hydrogen or, when n is 1, $R_5$ taken together with $R_3$ comprises a double bond; m is 1, 2 or 3; n is 0 or 1, and p is 0, 1 or 2.

28. A process as claimed in claim 1 wherein m is 1, n is 0, p is 1, $R_1$ and $R_2$ are each methyl and $R_3$ and $R_4$ are each hydrogen.

29. A process as claimed in claim 1 wherein X is a $C_{1-6}$ alkyl group or a phenyl or benzyl group, in each case optionally substituted by one or more substituents selected from $C_{1-6}$ alkyl, $C_{1-6}$ alkoxy, nitro, amino, $(C_{1-6})$alkylamino, di$(C_{1-6})$alkylamino, thio$(C_{1-6})$alkyl or phenyl substituents.

30. A process as claimed in claim 29 wherein X is a $C_{1-6}$alkyl group optionally substituted by one or more substituents selected from $C_{1-6}$alkoxy, nitro, amino, $(C_{1-6})$ alkylamino, di$(C_{1-6})$alkylamino or thio$(C_{1-6})$alkyl.

31. A process as claimed in claim 30 wherein X is tert-butyl.

32. A process as claimed in claim 1 wherein $R_6$ is bromo.

33. A process as claimed in claim 12 wherein $R_8$ is MgBr.

34. A process as claimed in claim 21 wherein $R_9$ is bromo.

35. A process for producing 8-[2'-(2(1)-tert-butyl-2H-tetrazol-5-yl)-biphenyl-4-yl-methyl]-2,4-dimethyl-5,8-dihydro-6H-pyrido[2,3-d]pyrimidin-7-one (or such a compound wherein a benzyl or p-methoxybenzyl group is present in place of the tert-butyl group) or a salt thereof, said process characterized in (A) reacting 2-tert-butyl-5-(2-bromo- or iodophenyl)-2H-tetrazole with magnesium to yield the bromo or iodo [2-[2-(tert-butyl)-2H-tetrazol-5-yl]phenyl]magnesium Grignard reagent, (B) transmetallizing said Grignard reagent with zinc chloride or zinc bromide; and (C) reacting the transmetallized product with 8-[(4-bromo-, iodo- or trisilylphenyl)-methyl]-5,8-dihydro-2, 4-dimethyl-pyrido[2,3-d]pyrimidin-7(6H)-one in the presence of a palladium or nickel catalyst to yield the product;
wherein throughout the process a benzyl or p-methoxybenzyl group may be present in place of the tert-butyl group.

36. A process according to claim 35 wherein the tert-butyl group is used.

37. A process according to claim 36 wherein 2-tert-butyl-5-(2-bromophenyl)-2H-tetrazole is used in step A.

38. A process according to claim 35 wherein zinc chloride is the transmetallizing agent in step C.

39. A process according to claim 35 wherein 8-[(4-bromophenyl)-methyl]5,8-dihydro-2,4-dimethyl-pyrido[2, 3-d]pyrimidin-7(6H-one is reacted with chloro or bromo[2-[2-(tert-butyl)-2H-tetrazol-5-yl]phenyl]zinc in step C.

40. A process according to claim 35 wherein a palladium catalyst is used in step C.

41. A process according to claim 40 wherein the palladium catalyst is generated from Pd(OAc)$_2$ or PdCl$_2$(PPh$_3$)$_2$ and an additive selected from the group consisting of PPh$_3$, P(o-tolyl)$_3$, P(t-butyl)$_3$, P(2-furyl)$_3$, P(OiPr)$_3$, CuI, CuBr, AsPh$_3$ and DIBAL.

42. A process according to claim 39 wherein the palladium catalyst is generated in the reaction vessel containing the chloro or bromo[2-[2-(tert-butyl)-2H-tetrazol-5-yl] phenyl]zinc.

43. A process according to claim 35 wherein the reaction of steps B and C and the generation of the palladium or nickel catalyst, with or without an additive, are carried out in the same reaction vessel.

44. A process as claimed in claim 35 comprising the further step of deprotecting the product to provide 8-[2'-(1H -tetrazol-5-yl)-biphenyl-4-yl-methyl]-2,4-dimethyl-5,8-dihydro-6H-pyrido[2,3-d]pyrimidin-7-one or a salt thereof.

45. A process for producing 8-[2'-(2(1)-tert-butyl-2H-tetrazol-5-yl)-biphenyl-4-yl-methyl]-2,4-dimethyl-5,8-dihydro-6H-pyrido[2,3-d]pyrimidin-7-one (or such a compound wherein a benzyl or p-methoxybenzyl group is present in place of the tert-butyl group) or a salt thereof, said process characterized in (B) transmetallizing bromo[2-[2-(tert-butyl)-2H-tetrazol-5-yl]phenyl]magnesium Grignard reagent with zinc chloride; and (C) reacting the transmetallized product with 8-[(4-bromophenyl)-methyl]5,8-dihydro-2,4-dimethyl-pyrido[2,3-d]pyrimidin-7(6H-one in the presence of a palladium catalyst to yield the product;

wherein throughout the process a benzyl or p-methoxybenzyl group may be present in place of the tert-butyl group.

46. A process as claimed in claim 45 comprising the further step of deprotecting the product to provide 8-[2'-(1H-tetrazol-5-yl)-biphenyl-4-yl-methyl]-2,4-dimethyl-5,8-dihydro-6H-pyrido[2,3-d]pyrimidin7-one or a salt thereof.

* * * * *

UNITED STATES PATENT AND TRADEMARK OFFICE
CERTIFICATE OF CORRECTION

PATENT NO. : 5,760,220
DATED : June 2, 1998
INVENTOR(S) : Pierre Giguere, et al.

It is certified that error appears in the above-indentified patent and that said Letters Patent is hereby corrected as shown below:

On the title page, insert item [63]:

Continuation-in-part of Ser. No. 08/478,592, Jun. 7, 1995, abandoned.

Signed and Sealed this

Eleventh Day of August 1998

*Attest:*

BRUCE LEHMAN

*Attesting Officer*  *Commissioner of Patents and Trademarks*